(12) United States Patent
Homan

(10) Patent No.: US 12,121,638 B2
(45) Date of Patent: Oct. 22, 2024

(54) METHOD AND DEVICE FOR CONTROLLING ODOR AND VAPOR

(71) Applicant: Gary Homan, Beaverton, MI (US)

(72) Inventor: Gary Homan, Beaverton, MI (US)

( * ) Notice: Subject to any disclaimer, the term of this patent is extended or adjusted under 35 U.S.C. 154(b) by 0 days.

(21) Appl. No.: 18/152,935

(22) Filed: Jan. 11, 2023

(65) Prior Publication Data

US 2024/0226363 A1   Jul. 11, 2024

(51) Int. Cl.
*A61L 9/14* (2006.01)
*B01D 53/14* (2006.01)
*E03F 5/10* (2006.01)

(52) U.S. Cl.
CPC .......... *A61L 9/145* (2013.01); *B01D 53/1493* (2013.01); *E03F 5/106* (2013.01); *B01D 2252/205* (2013.01)

(58) Field of Classification Search
CPC ................ A61L 9/145; B01D 53/1493; B01D 2252/205; E03F 5/106
See application file for complete search history.

(56) References Cited

U.S. PATENT DOCUMENTS

| | | | |
|---|---|---|---|
| 6,095,720 A | 8/2000 | Stark | |
| 6,845,527 B1 | 1/2005 | Kohn | |
| 7,344,579 B2 | 3/2008 | Chen | |
| 8,943,619 B2 | 2/2015 | Romero | |
| 10,106,966 B2 | 10/2018 | Cole | |
| 10,112,855 B2* | 10/2018 | Malone | ................... C02F 3/087 |
| 10,480,803 B2 | 11/2019 | Hatton et al. | |
| 10,690,636 B2 | 6/2020 | Ruppel et al. | |
| 2008/0292494 A1* | 11/2008 | Garvey | ..................... A61L 9/16 |
| | | | 422/4 |
| 2014/0332452 A1* | 11/2014 | Wacome | ............... E03F 5/0404 |
| | | | 210/170.03 |

* cited by examiner

*Primary Examiner* — Sean E Conley
*Assistant Examiner* — Brendan A Hensel

(57) ABSTRACT

A method of controlling vapor emissions using a liquid vapor trap containing an effective amount of a barrier fluid that will greatly reduce the volume of noxious and/or other gases emitted from a containment (natural or man-made) into the atmosphere. Examples of containment include, but are not limited to, septic, fossil fuels and landfills.

5 Claims, 5 Drawing Sheets

Figure 5

TABLE 1

Figure 1:
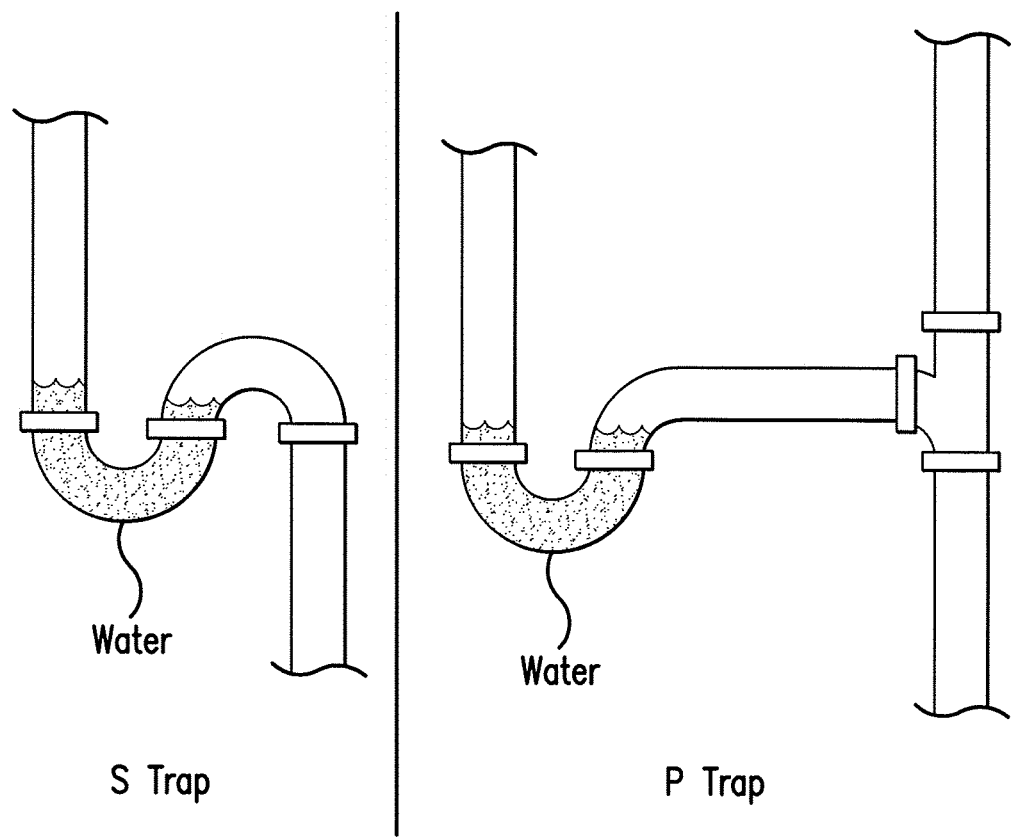

| Fluid | Fluid Level. (Cm) | Escape Pressure (WC) |
|---|---|---|
| 1 | 1.0 | 1.6 |
| 1 | 3.0 | 2.4 |
| 2 | 1.0 | 1.4 |
| 2 | 3.0 | 2.1 |
| 3 | 1.0 | 1.2 |
| 3 | 3.0 | 1.9 |
| Water | 1.0 | 1.0 |
| Water | 3.0 | 1.7 |

METHOD AND DEVICE FOR CONTROLLING ODOR AND VAPOR

CROSS-REFERENCE TO RELATED APPLICATIONS

Not Applicable.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

BACKGROUND OF THE INVENTION

This is an invention for a trap device containing an effective amount of a barrier fluid that will greatly reduce the volume of noxious and/or other gases emitted from a containment (natural or man-made) into the atmosphere. Examples of containment include, but are not limited to septic, fossil fuels and landfills.

Today our planet is undergoing changes in atmospheric conditions which could potentially alter weather patterns and air quality.

Scientists and governments worldwide have purported that unabated emission of gases and vapors from natural and man-made sources may be a major contributor to harmful atmospheric changes. There are many methods known in the art to help modulate or control the emission of gases into the atmosphere. However, most of these methods use highly sophisticated and expensive equipment to achieve desirable goals.

The instant invention provides a safe, effective and potentially economical means to dramatically reduce unabated gas and vapor emissions into our atmosphere while maintaining functionality in extreme weather conditions.

Known to the inventor herein, is U.S. Pat. No. 6,095,720, that issued Aug. 1, 2000, to Stark in which stabilized fluid barrier members are disclosed. The fluid barriers are sheet materials.

U.S. Pat. No. 6,845,527 that issued on Jan. 25, 2005, to Kohn discloses in-wall plumbing traps having integral connections for waste and vent lines.

A pipe trap comprising a body, a disc filter, a pipe and a plurality of mesh filters suitable for filtering gases is provided in U.S. Pat. No. 7,344,579, that issued Mar. 18, 2008, to Chen.

U.S. Pat. No. 8,943,619 that issued on Feb. 3, 2015, to Romero deals with a trap for positioning within a wall urinal.

U.S. Pat. No. 10,106,966 that issued Oct. 23, 2018, to IPS Corporation discloses the use of a air admittance valve which when subjected to a negative pressure condition vents a pipe system to an ambient environment.

A vapor management system is disclosed in U.S. Pat. No. 10,480,803 that issued Nov. 19, 2019, to Hatton et. al. and U.S. Pat. No. 10,690,636 that issued Jun. 23, 2020, to PerkinElmer Health Sciences, Inc. deals with a trap that can be used with chromatography systems.

None of the prior art references deal with a method or device of this invention.

THE INVENTION

Thus, in one embodiment what is disclosed and claimed herein is a method of controlling vapor emissions using a liquid vapor trap and a specific barrier fluid. The method comprises providing a liquid vapor trap and providing the liquid vapor trap with a barrier fluid such that vapors must pass through the barrier fluid.

The barrier fluid is selected from the group consisting of silicone fluids and organic fluids, and the barrier fluids have the following properties: melt transition temperature of less than $-25°$ C.; a vapor pressure of less than 20 mm mercury at $40°$ C.; and a viscosity of 1 to 10,000 centipoise at $25°$ C.

Further contemplated within the scope of this invention is a barrier fluid having a specific gravity of less than 1 and a barrier fluid having a goniometric static surface water contact angle of greater than 100 degrees.

An additional embodiment of this invention is a device for use with a barrier fluid to control the escape of gases and vapors.

Thus, such additional embodiment is a trap to control gas and vapor emissions. The trap comprises a first housing wherein the first housing has vertical walls, a bottom with an entry port for gases and vapors and a top with an exit port for gases and vapors.

There is a secondary housing mounted in an interior of the first housing, the secondary housing having partial vertical walls that do not rest on a bottom of the first housing. There is a water trap located in a bottom of the first housing which contains a siphon tube extending from the water trap to an exit from the first housing.

There is a secondary port through the secondary housing and a barrier fluid contained in the first housing wherein the volume of the barrier fluid exceeds a bottom edge of the partial walls of the secondary housing.

BRIEF SUMMARY OF THE INVENTION

The present invention uniquely combines a trap devise in situ in a containment vent with an effective amount of a specifically characterized barrier fluid to dramatically reduce the amount of noxious or greenhouse gases into the atmosphere, or into an external environment.

In its simplest form this invention can utilize an S-Trap or P-trap devise configuration well known in the plumbing and HVAC industries, along with the uniquely defined barrier fluid which allows for positive pressure venting but prevents gases from unabatedly escaping containment areas. The amount of positive pressure within the containment can be regulated by viscosity and depth of the barrier fluid within the trap devise installed in the vent line.

The trap device can also be optionally configured with a siphon and/or drain tube configuration to allow for the expulsion of any water contamination, whether direct from exposure or from condensation in the trap device or formed within the vent line.

The present invention sets a scope on the specifications of the barrier fluid used in combination with multiple design trap device options. The barrier fluids used in this invention must remain in the liquid state at very low temperatures to prevent total vent blockage and over-pressurization, and resist evaporation at high temperatures to maintain long-term functionality in extreme weather conditions.

BRIEF DESCRIPTION OF THE SEVERAL VIEWS OF THE DRAWING(S)

Figure 2:
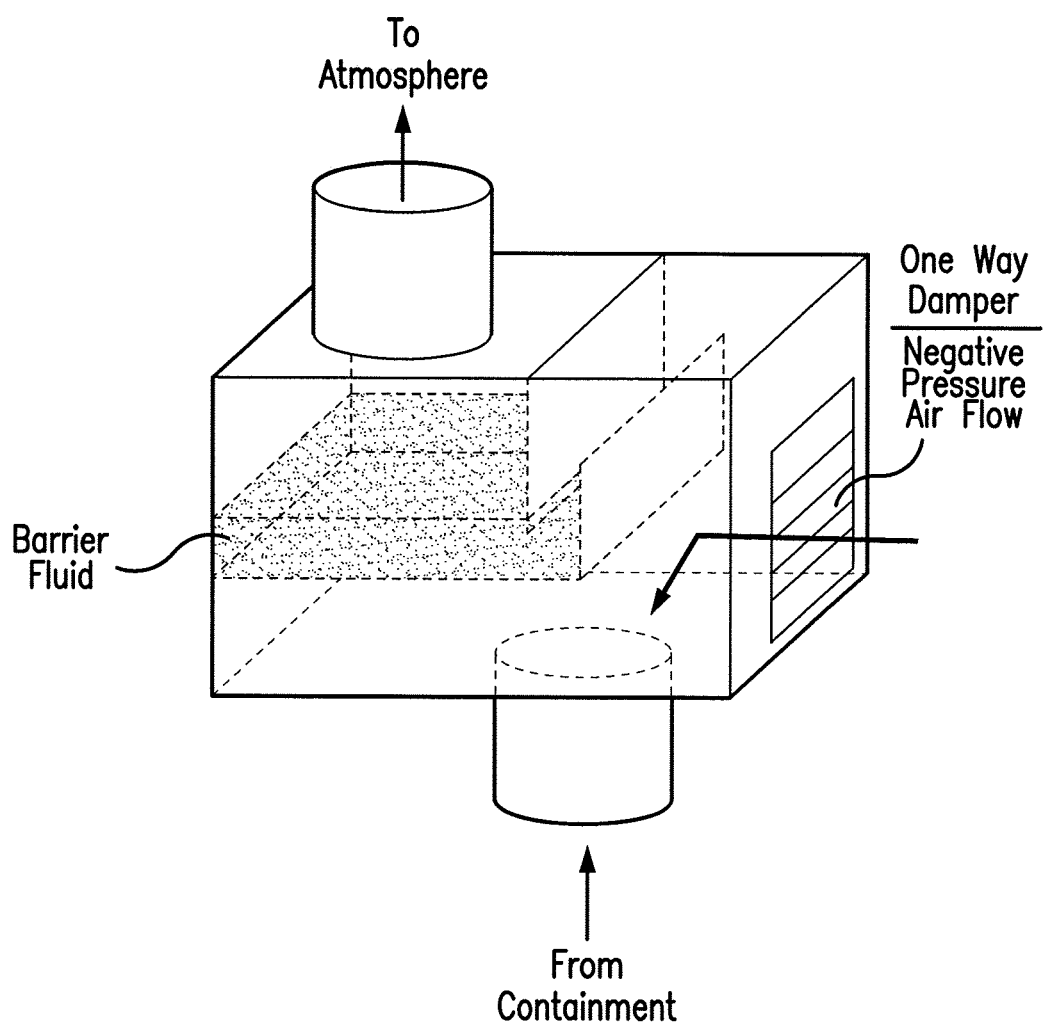
Figure 3:
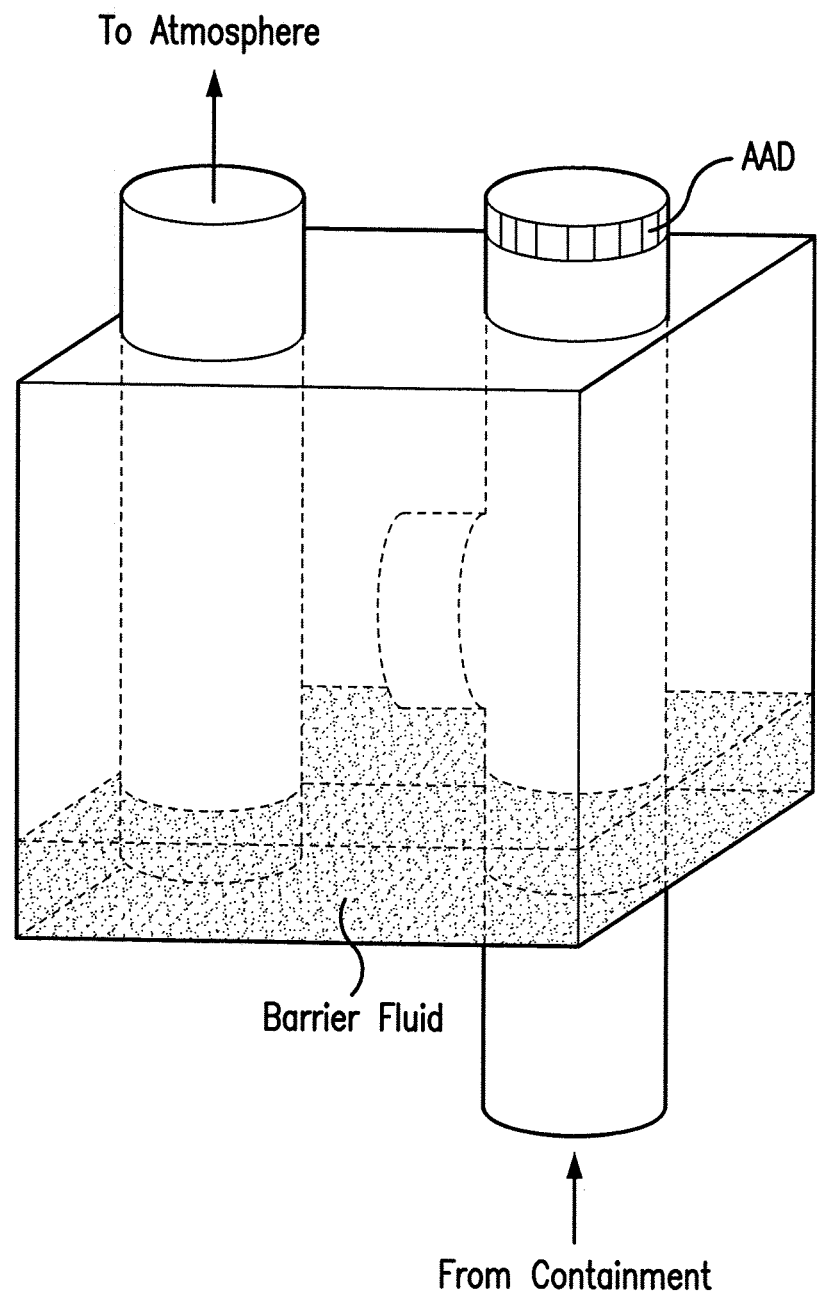
Figure 4:
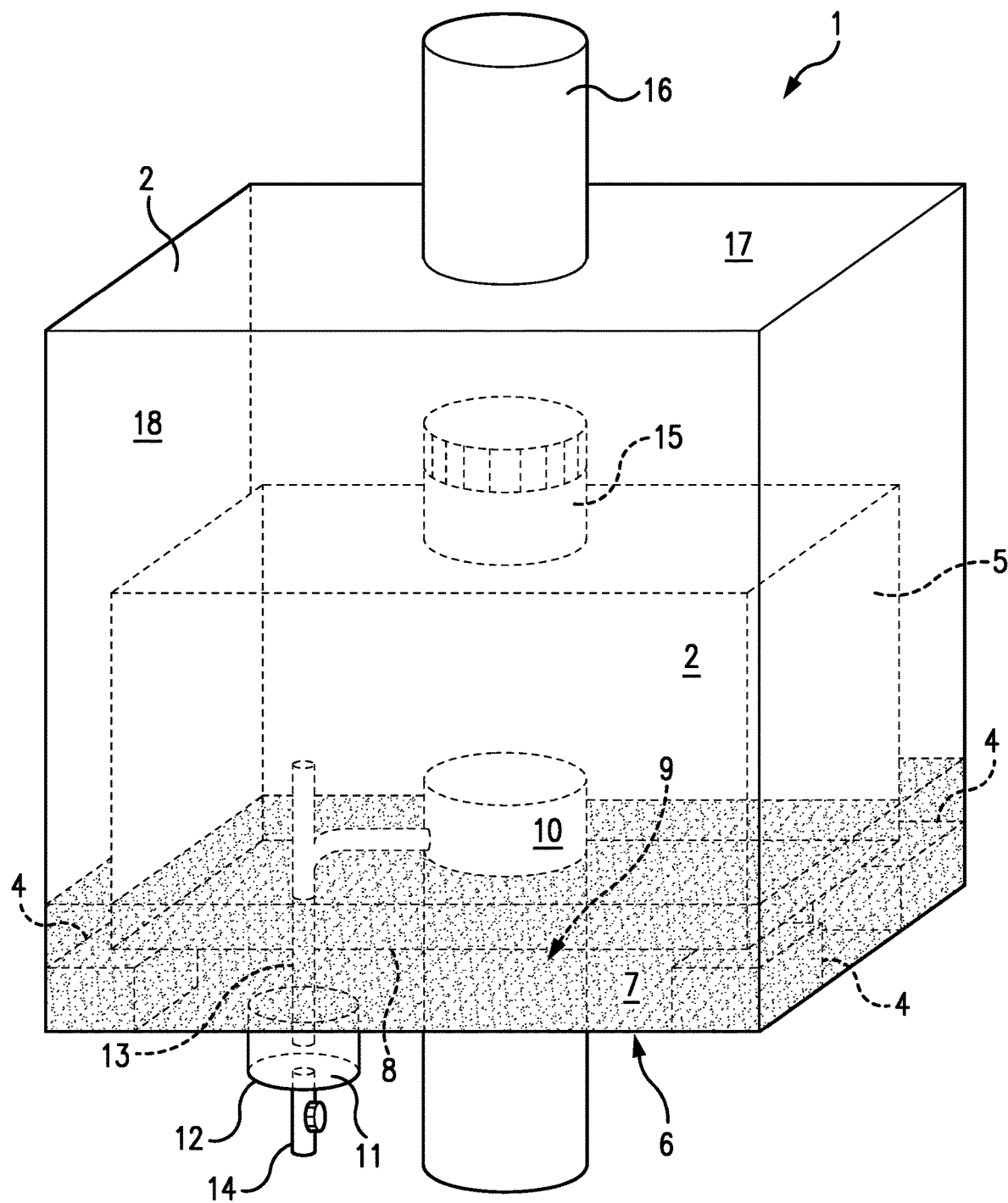

FIG. 1 is prior art S and P traps.
FIG. 2 is an illustration of one form of a trap device.
FIG. 3 is an illustration of another form of a trap device.
FIG. 4 is a full front view of a device of this invention.
FIG. 5 is Table I.

DETAILED DESCRIPTION OF THE INVENTION AND DRAWINGS

The present invention is comprised of two components, a trap devise and a barrier fluid. The trap devise may use any of the configurations known in the industry for trapping gases when water is the barrier fluid. These trap device configurations, if used with an "effective amount" of the barrier fluid defined below, would be inclusive of the present invention. An "effective amount" of barrier fluid is defined as the volume of fluid necessary to restrict continuous gas or vapor ventilation through the trap.

Gases and vapor include, but are not limited to, methane, carbon dioxide, flammable vapors and sulfur containing gases.

The trap can be configured at the entry, exit or anywhere within the vent line to reduce the flow of gases or vapors from the containment.

Method applications for the present invention include but are not limited to vent lines connected to the following containments: residential septic systems, commercial or community sewage treatment systems, local or public landfills, petroleum and petrochemical storage and processing units, or pulp and paper storage and process units.

Historically, water traps are used for gas and vapor suppression because of the simplicity and low costs relative to mechanical or electronic pressure relief valves (PRV).

However, water traps are limited to near ambient environments because water will freeze to a solid at sustained temperatures at or below zero degrees centigrade and thus plug or seal off a vent line to render it ineffective and potentially dangerous.

Furthermore, water can evaporate at ambient temperature and evaporates more rapidly as environmental temperatures increase above ambient to eventually render the trap ineffective to contain gases and vapors.

The unique combination of the trap device with an effective amount of barrier fluid within the scope of the present invention allows for use in extreme weather conditions to provide a sustainable and effective gas and vapor trap at environmental temperatures ranging from −25 to +50 degrees centigrade. The physical and mechanical properties of the trap and an effective amount of barrier fluid in vent lines allows gas and vapor control in some of the most severe weather conditions on Earth.

The Barrier fluids in the present invention can be organic fluids or polysiloxane fluids, and have the following properties: a Melt Transition Temperature (Tm) less than −25 degrees centigrade, a Vapor Pressure (Vp) of less than 20 mm Mercury (Hg) at 40 degrees centigrade, a viscosity of 1 to 10,000 centipoise at 25 degrees centigrade and in certain situations, a Specific Gravity (SG) less than 1 at 25 degrees centigrade and a goniometric static surface water contact angle of greater than 100 degrees.

Polysiloxane fluid compositions used in the present invention are polymers which meet the aforementioned barrier fluid properties and can be generally described by the average formula

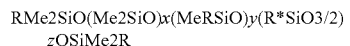

wherein Me denotes a methyl radical and R denotes a methyl radical, a hydroxyl radical, a phenyl radical, an alkyl radical with 2-6 carbon atoms, an alkenyl radical with 2-6 carbon atoms, a halogenated alkyl radical with 1 to 6 carbon atoms, or a silacyclopentene radical. R* can be the same as R, or represent a siloxane branch represented by the formula $RMe2SiO(Me2SiO)x-$. The average value of x and y can vary from 1 to 250, but preferably 5-100 and the value of z is from 0-10.

Organic fluid compositions used in the present invention are polymers which meet the aforementioned barrier fluid properties and may be a hydrocarbon oil, polyglycol oil, paraffinic oil, aromatic oil, or poly-alfa-olefinic oil as cited by Beretta, et al in U.S. Pat. No. 4,239,638.

The instant invention also allows for limited adjustments to the positive pressure necessary for the release of gases and vapors by adjusting the volume and/or the viscosity of the effective amount of barrier fluid used in the trap. For example, higher volumes and/or higher viscosities will equate to higher pressures before a release of gas or vapors occurs.

Examples of trap devices functional in the present invention may include but are not limited to those shown in FIGS. 2 and 3.

The most common trap device is often referred to as an S or P trap (FIG. 1) as demonstrated by Alexander Cummings in 1775, which laid the foundation for flush toilets. Other variations are shown in U.S. patents assigned to E. Riley in 1901 and J. E. Keyt in 1904. All of these devices used water as the barrier fluid.

A devise trap used in this invention can be optionally configured with one or more backdraft dampers, or Air Admittance Valves (AAV), which are commonly known in the arts, to provide air replacement if a negative pressure condition occurs within the vent line, but do not allow gases or vapors to escape the trap device in neutral or limited positive pressure conditions.

The Specific Gravity (SG) and the goniometric static surface water contact angle of the barrier fluid used in the instant invention uniquely provides the ability to remove water contamination due to direct exposure or condensation when the device trap further contains a siphon tube or water trap portal.

Water will separate from the barrier fluid, separate and sink, and concentrate in the trap at the bottom of the devise trap for continuous removal via a siphon tube or manually extracted via a water trap portal.

Optionally, a glycol, with a Specific gravity (SG) of greater than 1, and which is immiscible with the barrier fluid, may be added to prevent the water from freezing at temperatures below zero degrees centigrade.

Turning now to FIG. 4, there is shown a full front view of a device 1 of this invention. The device 1 has a first housing 2, which is a liquid leak proof cabinet. In the interior of the first housing 2 is a secondary housing 3 that in this Figure is mounted on four corner stanchions 4. This mode of suspending the secondary housing 3 within the first housing 2 is not the only method by which the secondary housing 3 can be maintained in the interior of the first housing 2. This can be achieved, for example, by suspension wires or strings.

It should be noted that the side walls 5 of the secondary housing 3 do not reach the bottom 6 of the first housing 2 but are somewhat short of the bottom 6. This configuration allows the barrier fluid 7 to circulate throughout the bottom 6 of the first housing 2 and in operation, there is enough volume of the barrier fluid 7 to come up above the bottom edge 8 of the side walls 5 of the secondary housing 3.

The bottom 6 of the first housing 2 has an opening 9 in the bottom 6 and situated in the opening 9 is a standpipe 10 which inserts into the secondary housing 3. The bottom 6 of the first housing 2 contains a water trap 11 and there is a stopcock 14 built into the bottom 12 of the water trap 11 that allows one to drain any water accumulated in the trap 11. Situated in the water trap 11 is a siphon tube 13, which extends into the standpipe 10 to allow excess water to be placed back in the standpipe 10 and its related system.

There is a secondary port 15 through the top of the secondary housing 3 and in an alternative embodiment, there can be an air admittance valve 19 covering the secondary port 15. There is an exit port 16 in the top 17 of the first housing 2 to allow for the escape of gas or vapors that penetrate and exit the barrier fluid. In addition to the top 17 of the first housing 2, there is also shown side walls 18.

In operation, when gas or vapors exit from the containment area, the gas or vapors enter the standpipe 10 and into the secondary housing 3 and are restricted by the barrier fluid 7 or the gases and vapors may develop higher pressures and exit the device 1 through the barrier fluid 7 and then into the first housing 2 and then out the exit pipe 16 in the first housing 2.

Example 1

A device prototype similar to that found in FIG. 4 was manufactured. The prototype was constructed with transparent polycarbonate to allow for experimental observations. A pressure gauge was mounted on the inner chamber and air pressure was introduced into the vapor inlet tube at the bottom of the trap device. The escape pressure in Table 1 was the amount of pressure in inches of water (WC) at 25 degrees centigrade for an air bubble to penetrate the barrier fluid.

Three fluids with properties within the scope of this invention were used in this example. Fluid 1 and fluid 2 were organic hydrocarbon polymers with viscosities of 2,350 cps and 420 cps, respectively. Fluid 3 was a polydimethylsiloxane with a viscosity of 50 cps. Water, which is not within the scope of this invention, was used for comparative purposes.

Fluid level was measured from the bottom edge of the inner chamber to the top of the barrier fluid in centimeters. See Table 1.

The data shown in Table 1 demonstrates the capability of the instant invention to be used in applications requiring varying amounts of pressure before the contained vapors breach the barrier fluid and exit via the outlet tube.

Example 2

A homeowner and neighbors reported strong sewer gas odors coming from a sewer vent pipe since construction of the home 5 years prior. The contractor attempted to eliminate the odors by extending the vent pipe above the roof peak. This was not successful, and the odor persisted. The prototype from Example 1 was attached to the top of the 3-inch vent pipe. The odor was no longer emitted freely into the atmosphere. Furthermore, the homeowner has not experienced any problems draining his sinks, tubs and the flushing of toilets. This demonstrates the functionality of the present invention to greatly reduce the volume of noxious vapors from entering the environment while providing a controllable pressure release of a containment.

Due to the functionality of the present invention in severe weather conditions, the homeowner has continued to see dramatic reductions of noxious odors throughout the year.

Based on the results of the Example, it would be expected to perform similarly when used on vent lines in waste landfills to dramatically reduce the amount of unabated greenhouse gas emissions while still providing controllable pressure relief. The negative pressure relief via the AAD and the controllable pressure relief (burping) of the barrier fluid will permit the landfill to continue decomposition processes while significantly reducing greenhouse gas emissions.

The present invention can also be used to limit the release of flammable vapors from a containment to reduce the risk of fires, or to facilitate controlled burns in petroleum and petrochemical applications.

What is claimed is:

1. A trap to control gas and vapor emissions, said trap comprising:
   A) a first housing, said first housing having an entry port for gases and vapors, a top, sides, and bottom;
   B) a secondary housing mounted in an interior of said first housing, said secondary housing having partial vertical walls that do not rest on a bottom of said first housing;
   C) a water trap located in a bottom of said first housing;
   D) an exit port through said top of said first housing;
   E) a siphon tube extending from said water trap to said exit of said first housing;
   F) a barrier fluid contained in said first housing wherein the volume of said barrier fluid exceeds a bottom edge of said partial walls of said secondary housing wherein said barrier fluid is selected from the group consisting of:
      a) an organic fluid composition selected from the group consisting of:
         i) hydrocarbon oil,
         ii) polyglycol oil,
         iii) paraffinic oil,
         iv) aromatic oil, and
         v) poly-alfa-olefinic oil;
      b) polysiloxane fluid polymer compositions having the average formula

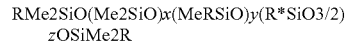

RMe2SiO(Me2SiO)$x$(MeRSiO)$y$(R*SiO3/2)
         $z$OSiMe2R wherein Me denotes a methyl radical and R denotes a methyl radical, a hydroxyl radical, a phenyl radical, an alkyl radical with 2-6 carbon atoms, an alkenyl radical with 2-6 carbon atoms, a halogenated alkyl radical with 1 to 6 carbon atoms, or a silacyclopentene radical; R* is the same as R, or represent a siloxane branch represented by the formula RMe2SiO(Me2SiO)x-; the average value of x and y varies from 1 to 250, and the value of z is from 0-10; wherein said barrier fluids have a Melt Transition Temperature (Tm) less than −25 degrees centigrade, a Vapor Pressure (Vp) of less than 20 mm Mercury (Hg) at 40 degrees centigrade, a viscosity of 1 to 10,000 centipoise at 25 degrees centigrade, a Specific Gravity (SG) of less than 1 at 25 degrees centigrade and a goniometric static surface water contact angle of greater than 100 degrees.

2. A trap as claimed in claim 1 wherein said secondary housing has as port covered with an air admittance valve.

3. A trap as claimed in claim 1 wherein said secondary housing is supported on stanchions.

4. A trap as claimed in claim 1 wherein a lower end of said water trap has affixed thereto a petcock.

5. The barrier fluid as claimed in claim 1 wherein the barrier fluid contains a polyglycol oil in the amount of 1 to 50 weight percent based on the amount of the barrier fluid.

* * * * *